United States Patent
Eldin et al.

(10) Patent No.: US 7,128,826 B2
(45) Date of Patent: Oct. 31, 2006

(54) POLYMERIZATION INHIBITOR FOR STYRENE DEHYDROGENATION UNITS

(75) Inventors: Sherif Eldin, Houston, TX (US); Ronnie L. Deason, Sulphur, LA (US); John Link, Humble, TX (US); Tiffany N. Morris, Leage City, TX (US)

(73) Assignee: General Electric Company, Schenectady, NY (US)

( * ) Notice: Subject to any disclaimer, the term of this patent is extended or adjusted under 35 U.S.C. 154(b) by 430 days.

(21) Appl. No.: 10/631,553

(22) Filed: Jul. 31, 2003

(65) Prior Publication Data

US 2005/0027150 A1   Feb. 3, 2005

(51) Int. Cl.
C10G 9/16 (2006.01)
C07C 7/04 (2006.01)
C07C 2/64 (2006.01)

(52) U.S. Cl. .................. 208/48 AA; 585/440; 585/950; 203/8; 203/9

(58) Field of Classification Search ........... 208/48 AA; 585/440, 950; 203/8, 9
See application file for complete search history.

(56) References Cited

U.S. PATENT DOCUMENTS

| | | | |
|---|---|---|---|
| 4,003,800 A * | 1/1977 | Bacha et al. .................... 203/9 |
| 4,032,547 A | 6/1977 | Bacha et al. |
| 4,628,136 A | 12/1986 | Sardina |
| 5,358,698 A | 10/1994 | Butler et al. |
| 5,396,004 A * | 3/1995 | Arhancet et al. .............. 585/5 |
| 5,446,220 A | 8/1995 | Arhancet |
| 5,489,720 A | 2/1996 | Arhancet |
| 5,616,774 A | 4/1997 | Evans et al. |
| 5,648,572 A | 7/1997 | Arhancet et al. |
| 5,648,573 A | 7/1997 | Arhancet et al. |
| 6,024,894 A | 2/2000 | Arhancet |
| 6,388,155 B1 | 5/2002 | Sy et al. |
| 6,926,820 B1 * | 8/2005 | Eldin et al. .............. 208/48 AA |
| 2004/0010159 A1 * | 1/2004 | Benage ........................ 558/306 |
| 2005/0113626 A1 * | 5/2005 | Benage et al. .............. 585/950 |

FOREIGN PATENT DOCUMENTS

WO   WO 98/02403 A1   1/1998

OTHER PUBLICATIONS

Zolotova et al., Rate Constants of the Reaction of Methylenequinones with Alkyl Hydrocarbon Radicals, pp. 41-46, translated from Kinetika i Kataliz, vol. 20, No. 1, pp. 56-61, Jan.-Feb. 1979, Plenum Publishing Corporation.

Zolotova et al., Reactivity of Methylenequinones as Inhibitors of the Liquid-Phase Oxidation of Hydrocarbons, pp. 34-40, translated from Kinetika i Kataliz, vol. 20, No. 1, pp. 48-55, Jan.-Feb. 1979, Plenum Publishing Corporation.

Ershov et al., Stable Methylenequinones, pp. 888-890, translated from Izvestiqa Akademii Nauk SSSR, Seriya Khimicheskaya, No. 5, pp. 928-930.

Chiang et al., Reactive Intermediates. Some Chemistry of Quinone Methides, Pure Appl. Chem., 2000, pp. 2299-2308, vol. 72, No. 12.

Volok'Kin et al., Stable Methylenequinones, Russina Chemical Reviews, 1988, pp. 336-349, vol. 47, No. 4, translated from Uspekhi Khimii, vol. 57, pp. 595-624.

\* cited by examiner

*Primary Examiner*—Thuan D. Dang
(74) *Attorney, Agent, or Firm*—Wegman, Hessler & Vanderburg

(57) ABSTRACT

Quinone methide derivatives such as 4-benzylidene-2,6-di-tert-butyl-cyclohexa-2,5 dienone are used to inhibit styrene monomer polymerization in the dehydrogenator portion of a styrene monomer production system. The inhibitor contacts the dehydrogenation effluent and does not partition in substantial amounts to the aqueous phase that is separated in the phase separator.

10 Claims, 1 Drawing Sheet

POLYMERIZATION INHIBITOR FOR STYRENE DEHYDROGENATION UNITS

FIELD OF THE INVENTION

Figure 1:
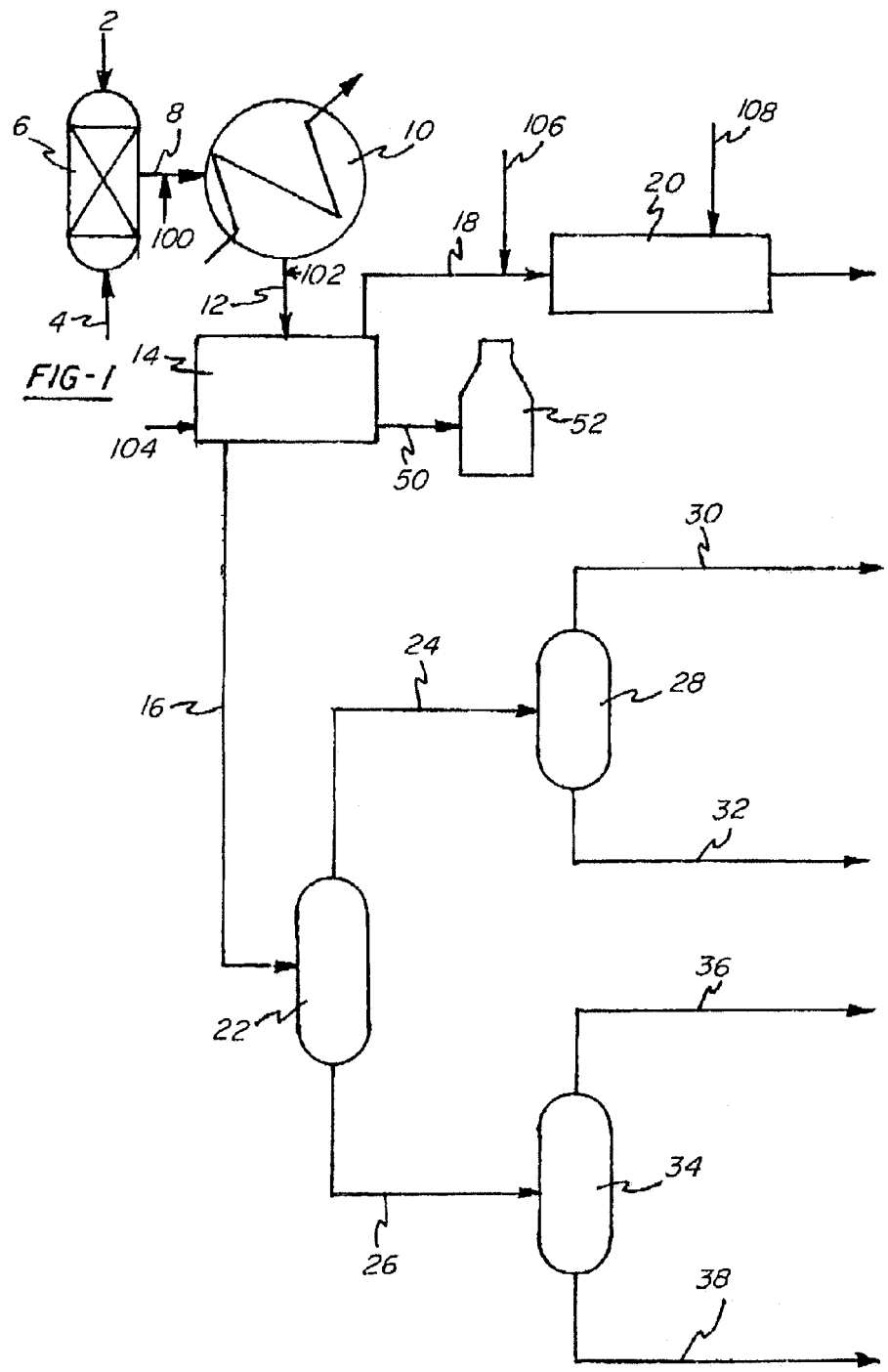

The invention pertains to polymerization inhibition methods wherein styrene monomer is inhibited from polymerizing by a use of polymerization inhibitor brought into contact with the dehydrogenation gas stream in ethylbenzene dehydrogenation sections of styrene monomer production processes.

BACKGROUND

Styrene monomer is typically produced from ethylbenzene at temperatures from about 600° C. and higher by vapor phase catalytic dehydrogenation in the presence of steam. Known catalysts include palladium oxide, platinum metal, molybdenum-bismuth oxide and oxides of copper, zinc, arsenic, antimony, chromium, iron, and cobalt.

The hot gaseous effluent from the dehydrogenator contains primarily styrene, hydrogen, unreacted ethylbenzene, divinylbenzene water, and minor amounts of benzene, toluene, methane, ethane, carbon monoxide, carbon dioxide, and various polymeric components. The effluent gas from the dehydrogenation reactor may be partially cooled in a waste heat exchanger or the like and then is typically fed to a condenser wherein styrene, unreacted ethylbenzene, divinylbenzene, sundry polymeric materials and the aqueous component are condensed with the hydrogen, methane, ethane, carbon monoxide and dioxide and the benzene and toluene remaining in the gas phase.

The partially condensed effluent is next fed to the phase separator wherein the gas phase is separated and subsequently treated to recover benzene and toluene. The aqueous phase is separated and, in most cases, is used as boiler feedwater. The hydrocarbon phase comprising styrene monomer and ethylbenzene is then subjected to distillation or other purification processes for separating styrene monomer from the ethylbenzene.

In the purification or distillation process stream, polymerization inhibitors are commonly added to inhibit undesired styrene monomer polymerization. Examples of addition of polymerization inhibitors at the purification stage include: U.S. Pat. No. 6,024,894 (Arhancet) wherein a combination of quinone methides and hydroxylamine are used; and U.S. Pat. No. 4,003,800 (Bacha et al.) wherein quinone alkides are charged to the purification zone.

In addition to the desire to inhibit polymerization in the purification stage, styrene monomer polymerization may also occur at process locations upstream thereof. For example, the styrene monomer present in the hot dehydrogenation effluent may polymerize causing fouling of the condenser and separator equipment. In many cases, polymerization treatments that are effective when injected in the purification process do not function effectively as inhibitors in the dehydrogenation section of the process. These known inhibitors sometimes partition to the aqueous phase and are therefore not available to inhibit hydrocarbon phase styrene monomer polymerization in dehydrogenator process lines and equipment such as the main condenser and phase separator. Additionally, some inhibitors maybe carried as contaminants in the aqueous phase and, as such, are undesirable components of the aqueous phase as it may ultimately be used as boiler or other process feedwater.

SUMMARY OF THE INVENTION

The present invention is directed toward styrene monomer inhibition in the dehydrogenation section of styrene monomer production systems. In these systems, styrene monomer is produced via the dehydrogenation of ethylbenzene at elevated temperature and in the presence of steam. The dehydrogenation effluent from the dehydrogenation reactor is separated in a separator or settling drum into a gaseous phase comprising hydrocarbons, an aqueous phase comprising steam condensate, and an organic phase comprising styrene monomer and unreacted ethylbenzene. Styrene is distilled from the organic phase in a distillation or purification unit located downstream from the phase separator. In accordance with the invention, the dehydrogenation effluent is contacted with an effective amount for the purpose of a styrene monomer polymerization inhibitor comprising a quinone methide (QM) compound having the formula:

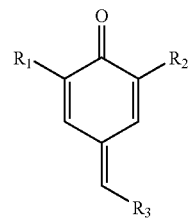

wherein $R_1$ and $R_2$ are independently H, $C_1$ to $C_{18}$ alkyl, $C_5$ to $C_{12}$ cycloalkyl; or $C_7$ to $C_{15}$ phenylalkyl, and $R_3$ is aryl, or aryl substituted with $C_1$ to $C_6$ alkyl, alkoxy, hydroxy, nitro, amino, carboxy or mixtures thereof.

The invention will be further described in conjunction with the appended drawing wherein:

DRAWING

FIG. 1 is a schematic process diagram of a typical styrene monomer production system.

DETAILED DESCRIPTION

Turning to the drawing FIGURE, this is a schematic process diagram showing a typical styrene monomer production system as set forth in U.S. Pat. No. 6,388,155 (Sy et al.). The entire content of the '155 patent is hereby incorporated by reference.

Dehydrogenation is usually carried out at about 660° C. or higher using low pressure and dilution steam. Liquid ethylbenzene is fed to dehydrogenator 6 via line 4 with steam being admitted at the top of the reactor as shown by reference numeral 2. Dehydrogenation effluent exits from the dehydrogenator along line 8 wherein it may be sent to condenser 10. The effluent gas from the dehydrogenation unit contains primarily styrene, hydrogen, unreacted ethylbenzene, divinylbenzene and small amounts of benzene, toluene, methane, ethane, carbon monoxide, carbon dioxide, various polymeric materials, and tars as well as an aqueous component. Prior to its passage to condenser 10, the effluent gas may be partially cooled in a waste heat exchanger or the like (not shown).

In the condenser, the styrene, unreacted ethylbenzene, divinylbenzene, polymeric materials, tars and aqueous components are condensed while the hydrogen, methane, ethane, and carbon monoxide and dioxide and most of the benzene and toluene remain in the gas phase. From the main condenser 10, the now partially condensed effluent is fed to the phase separator 14. The gaseous phase exits the separator via line 18 and may be treated by a compressor or the like 20 so as to recover benzene and toluene therefrom. The aqueous phase exits the separator 14 via line 50 wherein it may be fed to boiler 52.

The organic phase consisting primarily of styrene monomer and ethylbenzene exits the separator 14 via process line 16 and is passed to distillation or purification units shown schematically at 22, 28, and 34. Ethylbenzene and styrene monomer are isolated in the distillation unit 22 with the overhead ethylbenzene exiting from the distillation unit via line 44 wherein it is recovered in reactor 28. The styrene monomer distillate exits the unit 22 via a line 26 for further purification in reactor 34. In accordance with the invention, the styrene monomer polymerization inhibitor may be injected directly into the separator 14 as shown by feed line 104, or at any location upstream thereof such as in the effluent line 8 through feed line 100, condenser 10, or line 12 through feed line 102, or through inlets 106 or 108 to off gas compressor 10 or discharge cooler.

The QM styrene monomer polymerization inhibitor in accordance with the present invention does not substantially partition with the aqueous phase and therefore problems with regard to contamination of the aqueous phase exiting separator 14 via line 18 are minimized. In accordance with the invention, from about 1–1000 ppm of the styrene monomer polymerization inhibitor is added to make contact with the dehydrogenation effluent based on about one million parts of styrene monomer in the effluent. More preferably, the addition level for the polymerization inhibitor is from about 1–250 ppm.

The quinone methide derivatives used in accordance with the instant invention have the formula

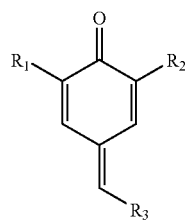

wherein $R_1$ and $R_2$ are independently H, $C_1$ to $C_{18}$ alkyl, $C_5$ to $C_{12}$ cycloalkyl; or $C_7$ to $C_{15}$ phenylalkyl, and $R_3$ is aryl, or aryl substituted with $C_1$ to $C_6$ alkyl, alkoxy, hydroxy, nitro, amino, carboxy or mixtures thereof. Means for preparing these compounds may be found in U.S. Pat. No. 4,032,547, the contents of which are wholly incorporated by reference herein. Preferably, the quinone methide derivative is 2,6-di-tert-butyl-4-benzylidene-cyclo-2,5-dienone.

The invention will now be described in conjunction with the following examples which should be viewed as being illustrative of the invention and should not be deemed to limit the invention in any manner.

EXAMPLES

Introduction

During styrene production, the hot ethylbenzene dehydrogenation reactor effluent is cooled, condensed, and sent to a settling drum. Non-condensables are compressed in the vent gas compressor and sent to the boilers to be used as fuel. Condensables are settled in a settling drum allowing for the separation of water and hydrocarbons containing crude styrene. The separated crude styrene is then sent to distillation for purification or to storage. The dehydrogenation effluent and non-condensables in the vent gas compressor are composed of water and hydrocarbon vapors containing styrene. The high temperatures to which the reactive monomer styrene is exposed causes styrene to polymerize. A number of known styrene polymerization inhibitors that are very effective in the distillation sections have limited applicability in the dehydrogenation section due to excessive temperatures and the presence of water. Many polymerization inhibitors partition to the water phase, reducing their ability to inhibit styrene polymerization in the hydrocarbon phase and contaminating the water.

In order to contrast the performance of the QM styrene dehydrogenation polymerization inhibitors with the prior art, N,N-dihydroxypropyl hydroxylamine (HPHA) was chosen as an example of a compound that is well known for its efficacy as a styrene monomer polymerization inhibitor in styrene monomer distillation or purification units. The performance of HPHA was contrasted to that of a quinone methide, namely: 4-benzylidene-2,6-di-tert-butyl-cyclohexa-2,5-dienone a water insoluble inhibitor. A first comparative test was undertaken to simulate conditions present in a styrene monomer purification system wherein the HPHA would be expected to perform well.

Styrene Reflux Studies

The two inhibitors were tested in a Styrene Reflux test wherein 25 ppm of HPHA or QM were added to styrene that was subjected to 85° C. temperatures for five hours. Results are reported in Table 1 and demonstrate that, as expected, HPHA performed better than QM in reducing % polystyrene formation.

TABLE 1

Styrene Reflux Test under Argon at 85° C.

| Time (min) | Polymer Blank | % Polymer HPHA (25 ppm) | % Polymer Quinone Methide (25 ppm) |
|---|---|---|---|
| 0 | 0 | 0 | 0 |
| 30 | 0.19 | 0 | 0.009 |
| 60 | 0.45 | 0 | 0.05 |
| 90 | 0.89 | 0 | 0.08 |
| 120 | 1.24 | 0 | 0.12 |
| 150 | 1.6 | 0.004 | 0.18 |
| 180 | 2.02 | 0.01 | 0.24 |
| 210 | 2.69 | 0.02 | 0.28 |
| 240 | 3.49 | 0.02 | 0.32 |
| 270 | | 0.05 | 0.38 |
| 300 | | 0.06 | 0.45 |

Dehydrogenation Conditions

Two separate tests were run under conditions that simulate the dehydrogenation unit. The first simulation test was a Styrene Polymerization Static Test. This test involved nitrogen-purging of test tubes containing 50 ppm HPHA or QM inhibitor in a mixture of water (25%), styrene (15%), and ethylbenzene (60%) at 90° C. for specified amounts of time ranging from one to five hours, followed by removing the heat, separating the two phases, and measuring % polystyrene in the hydrocarbon phase by methanol precipitation method. Table 2 demonstrates the unexpected enhanced performance of QM over HPHA in inhibiting styrene polymerization as shown by reduction in % polymer.

TABLE 2

Time vs. % Polymer for Styrene Static Polymerization Test with no Treatment Against 50 ppm of HPHA and Quinone Methide - Dehydrogenation Unit Conditions % Polymer

| Time (hour) | Blank | HPHA | Quinone Methide |
|---|---|---|---|
| 0 | 0.00 | 0.00 | 0.00 |
| 3 | 0.55 | 0.49 | 0.00 |
| 4 | 1.00 | 0.79 | 0.02 |
| 5 | 1.53 | 0.98 | 0.04 |

The second series of tests compared the performance of inhibitors in the presence of 20 ppm of the products containing HPHA and QM. A mixture of water (25%), styrene (15%), and ethylbenzene (60%) with different polymerization inhibitors, was purged with nitrogen then heated at 150° C. (reflux temperature 108° C.) for ten minutes with continuous stirring, followed by removing the heat and allowing the mixture to settle and cool to room temperature. The water and hydrocarbon phase were separated and % polystyrene in the hydrocarbon phase was measured by methanol precipitation method. The water phase polymer was below the detection limit, and the resulting % polymer in the hydrocarbon phase is listed below.

Another similar test was performed with 50 ppm of the treatments. Results are shown in Table 3 and 4. These results demonstrate the unexpected enhanced performance of QM over HPHA in inhibiting styrene polymerization, thereby reducing % polymer formed under dehydrogenation conditions.

TABLE 3

Time vs. % Polymer for Styrene Polymerization Reflux Tests with no Treatment Against 20 ppm of HPHA and Quinone Methide Solutions.

| Treatment (20 ppm product) | % Polymer |
|---|---|
| Blank | 7.9 |
| HPHA | 8.1 |
| Quinone Methide | 4.0 |

TABLE 4

% Polymer Styrene Polymerization Reflux Tests with no Treatment vs. 50 ppm of HPHA and QM.

| Treatment (ppm) | % polymer |
|---|---|
| Blank | 2.90 |
| HPHA (50 ppm) | 0.76 |
| QM (50 ppm) | 0.00 |

Phase separation tests were also undertaken. Generally, N,N-bis (hydroxypropyl) hydroxylamine—(HPHA) is the only inhibitor injected into the dehydrogenation unit of the separator system. HPHA is a water soluble inhibitor and, therefore, at the oil/water separator, no appreciable amount of styrene inhibitor is present in the organic phase. The present invention also encompasses use of the quinone methide (QM) dehydrogenation system styrene polymerization inhibitor in combination with traditional water based styrene polymerization inhibitors such as HPHA, Hydroxy-TEMPO, and DEHA. The QM inhibitor provides benefit by adding polymer inhibition in the organic phase and does not result in adverse phase implications.

Phase Separation Tests

The lab simulation process sample containing 20 ppm HPHA was used as the benchmark to compare against the combined product processed sample. HPHA was chosen as the base line since no adverse phase implications have been reported with regard to its use in the dehydrogenation unit separator system. Foaming and emulsion tendencies were observed and recorded during mixing and bench sit. Observations were recorded for the separation of the organic and aqueous phase after mixing, which correlates to the oil/water separator in styrene monomer production systems. The object is to see if the combination of QM oil soluble inhibitor and HPHA performs as well as or better to the HPHA alone with regard to adverse oil/water phase reactions or conditions.

An initial cold-dose bottle test was performed. Reagent grade styrene was filtered through the inhibitor column remover. The ratio of fluids at additive injection point is 60% water, 23% inhibitor-free styrene, and 17% ethylbenzene. These 3 components at given ratios were prepared in the 100 mL graduated-centrifuge tubes. The tubes were dosed accordingly with 1% HPHA (dil in water), and 20% QM (dil in toluene). The tubes were heated to 110° C. for ten minutes. They were removed from an oil bath and placed on a horizontal shaker on low speed for one minute. The tubes were removed, placed in a rack on the bench top and room temperature and observations recorded at time intervals.

The 20 ppm HPHA treatment and a treatment of 10 ppm HPHA and 10 ppm QM were also placed on a defoamer apparatus. The defoamer apparatus consists of a 500 mL graduated cylinder, special 4 hole glass top cap, sparging tube with nitrogen gas supply, thermocouple, and heating mantle. The special 4 hole cap allows the nitrogen sparging tube, thermocouple, pressure-off vent, and a septum-injection port for adding the additive. The appropriate ratio of water, inihibitor-free styrene, and ethylbenzene was prepared in the cylinder to achieve 259 mL of total sample. The sample was sparged with sufficient nitrogen to simulate process flow (vigorous rolling surface) and enable mixing of the organic and water phases. The sample was dosed with syringe through the septum when temperature was 105° C. Sample was observed for 10 minutes after dosing and for one hour during bench sit.

Results are reported below:

Cold Dose Results Summary

Blank vs. Baseline-Tube #1 i.e., 20 ppm HPHA

The blank and baseline-tube #1 (200 ppm HPHA) exhibited no differences in the organic or aqueous phases. In both the blank and basetube #1 here was 1–2 small pin-head sized water droplets on wall in upper organic layer at 1 min and thereafter. Water drop rate was the same for both, almost 100% of water in system separated within 1 minute after mixing. There was minimal (<0.1 ml) foam present from the mixing, which dissipated before first recorded observation at one minute. This comparison validates the current "no phase harm" applicability of 20 ppm HPHA in the customer's process.

Baseline Tube #1 (20 ppm HPHA) vs. Tube #2 (20 ppm QM)

QM alone was superior in phase separation than the baseline-tube #1. There was no water in upper organic layer. Both organic and aqueous phase were clearer in tube #2. Water drop and minimal foaming from mixing was identical to baseline and dissipated within one minute.

CONCLUSION

HPHA alone at 20 ppm, QM alone at 20 ppm, and the combination of 10 ppm HPHA plus 10 ppm QM exhibit no negative phase tendencies in either the organic or aqueous layers in the simulated matrix (60% water, 23% inhibitor-free styrene, and 17% ethylbenzene). This "no phase harm" for these three holds true for cold dose bottle testing, bench top oil/water separation stage and during foaming-apparatus when compared to the blank.

Accordingly, in another aspect of the invention, a combined styrene monomer polymerization inhibitor approach is provided that can be injected into process lines and equipment in the dehydrogenation section of the process without interfering with the separation of the hydrocarbon phase from the aqueous phase. Such phase separation interference is normally manifested in excessive foaming or emulsion formulation tendencies.

The combined treatment comprises a QM/HPHA product that be fed in the dehydrogenation section of the system, for example to any one of the feed lines 100, 102, 104, 106, or 108 as shown in the FIGURE. Preferably the components of the combined treatment are present in an amount of about 0.5–2 moles of QM: 1 mole of HPHA. Preferably, the components are present in a molar amount of 1 mole QM: 1 mole HPHA. Preferably, the combined treatment is fed to the requisite portion of the dehydrogenation section in an amount of about 1–250 ppm total inhibitor. At present, the most preferred combined treatment is fed at about 10 ppm QM and 10 ppm HPHA relative to the weight of styrene monomer present in the dehydrogenation effluent.

While we have shown and described herein certain embodiments of the invention, it is intended that these be covered as well any change or modification therein which may be made without departing from the spirit and scope of the invention as defined in the appended claims.

What is claimed is:

1. In a system for the production of styrene monomer by dehydrogenation of ethylbenzene in an upstream dehydrogenation unit of said system at elevated temperature and in the presence of steam wherein effluent from the dehydrogenation unit is formed that is subsequently separated in a phase separator located downstream from said dehydrogenation unit into a gaseous phase comprising hydrocarbons, an aqueous phase comprising steam condensate, and an organic phase comprising styrene monomer and unreacted ethylbenzene and wherein styrene is then distilled from said organic phase in a distillation unit located downstream from said phase separator, an improved method comprising contacting said effluent with an effective amount of a styrene monomer polymerization inhibitor (SMPI), wherein said SMPI comprises a quinone methide compound having the formula:

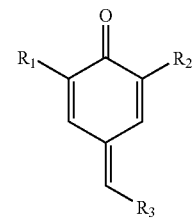

wherein $R_1$ and $R_2$ are independently H, $C_1$ to $C_{18}$ alkyl, $C_5$ to $C_{12}$ cycloalkyl; or $C_7$ to $C_{15}$ phenylalkyl, and $R_3$ is aryl, or aryl substituted with $C_1$ to $C_6$ alkyl, alkoxy, hydroxy, nitro, amino, carboxy or mixtures thereof.

2. Improved method as recited in claim 1 wherein from about 1–250 ppm of said SMPI is added to said dehydrogenation effluent based on 1 million parts of styrene monomer in said effluent.

3. Improved method as recited in claim 2 wherein from about 10–100 ppm of said SMPI is added to said dehydrogenation effluent based on 1 million parts of styrene monomer in said effluent.

4. Improved method as recited in claim 1 wherein said SMPI is 2,6-di-tert-butyl-4-benzylidene-cyclo-2,5-dienone.

5. Improved method as recited in claim 4 wherein said SMPI is fed into said phase separator in order to contact said dehydrogenation effluent.

6. Improved method as recited in claim 4 wherein said SMPI is fed into said system at a location at or upstream from said phase separator.

7. Improved method as recited in claim 6 wherein said dehydrogenation effluent comprises styrene monomer, unreacted ethylbenzene and water.

8. Improved method as recited in claim 5 wherein said dehydrogenation effluent comprises styrene monomer, unreacted ethylbenzene and water.

9. Improved method as recited in claim 1 further comprising contacting said effluent with an hydroxylamine present in an amount of 1–250 ppm based upon the amount of styrene monomer in said effluent.

10. Improved method as recited in claim 9 wherein said hydroxylamine is N,N-bis(hydroxypropyl) hydroxylamine (HPHA).

* * * * *